United States Patent [19]
Gable

[11] 3,987,678
[45] Oct. 26, 1976

[54] PNEUMATIC CONDENSER
[75] Inventor: Jack L. Gable, Bakersfield, Calif.
[73] Assignee: Superior Cotton Sampling, Inc., Calif.
[22] Filed: Feb. 20, 1976
[21] Appl. No.: 659,762

[52] U.S. Cl. .............................................. 73/422 R
[51] Int. Cl.² .......................................... G01N 1/02
[58] Field of Search ........ 73/421 R, 422 R, 422 TC, 73/423 R

[56] References Cited
UNITED STATES PATENTS

| | | | |
|---|---|---|---|
| 2,509,264 | 5/1950 | Cox | 73/422 R |
| 3,110,182 | 11/1963 | Moss et al. | 73/421 R |

Primary Examiner—S. Clement Swisher
Attorney, Agent, or Firm—Huebner & Worrel

[57] ABSTRACT

A pneumatic condenser particularly suited for use in periodically sampling raw cotton as the cotton is delivered to a bale press. The condenser is characterized by an extractor tube adapted to be connected to a cotton-delivery conduit and employed for periodically extracting batches of cotton from the conduit, a pneumatic catcher communicating with the extractor tube for serially collecting each extracted batch of raw cotton, and a pneumatic circuit for serially delivering each batch of raw cotton from the catcher to a sample press.

8 Claims, 4 Drawing Figures

U.S. Patent     Oct. 26, 1976     3,987,678
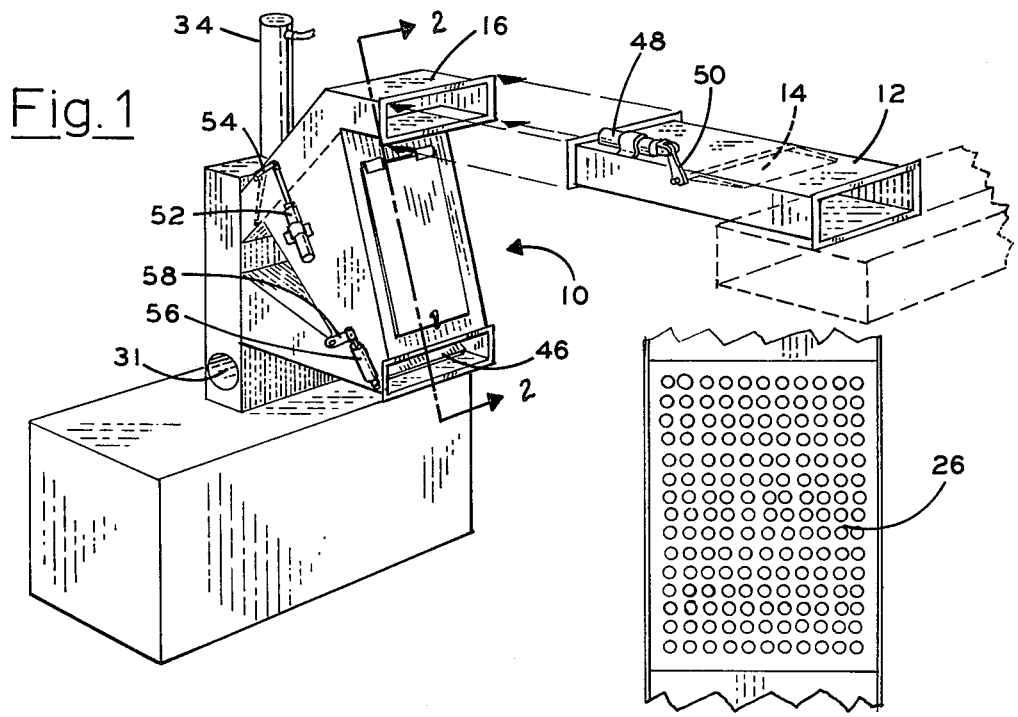
Fig. 1
Fig. 3
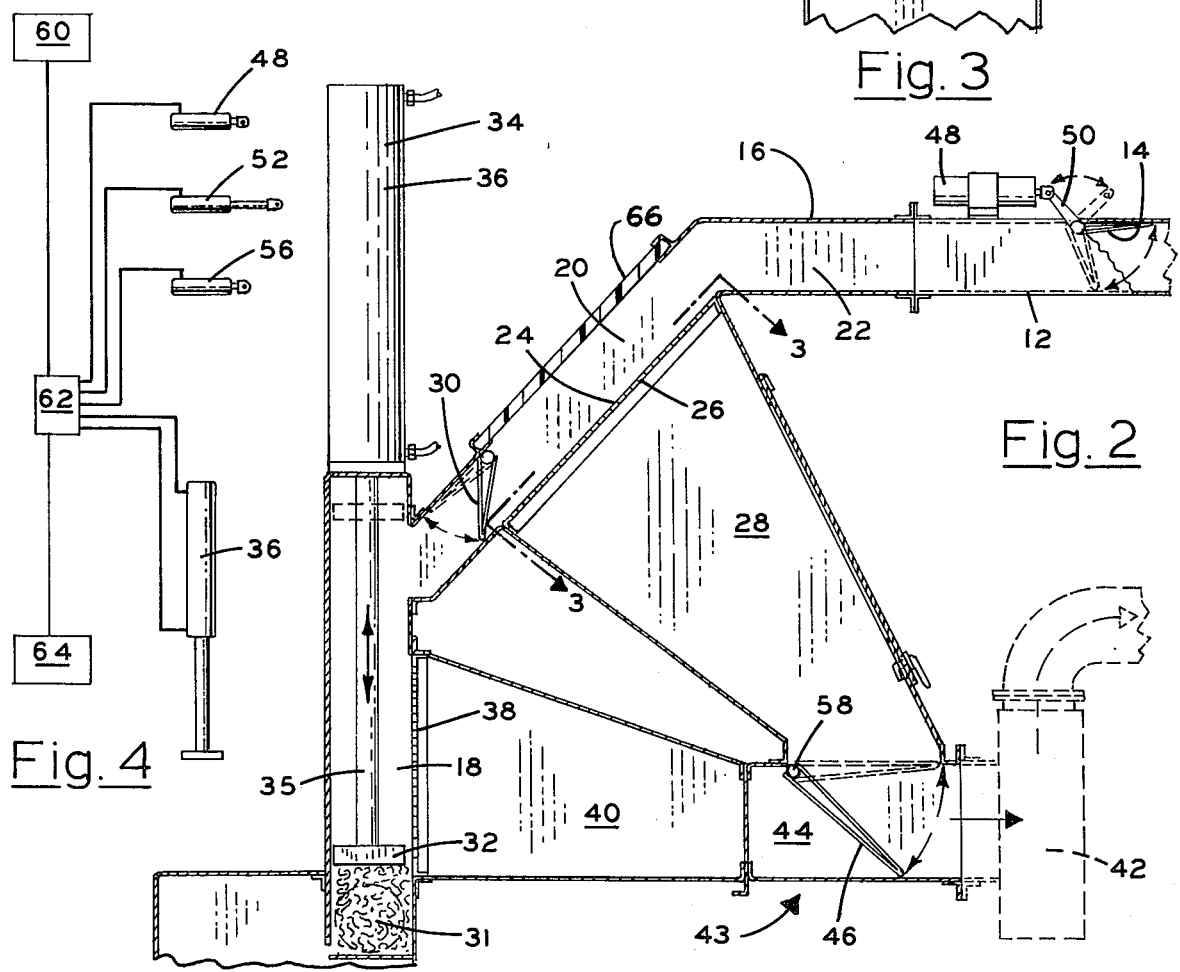
Fig. 4
Fig. 2

PNEUMATIC CONDENSER

BACKGROUND OF THE INVENTION

1. Field of the Invention

The invention generally relates to condensers of the type employed during ginning operations and more particularly to an improved pneumatic condenser particularly suited for use in automatically sampling raw cotton as the cotton is delivered to a bale press.

2. Description of the Prior Art

As can be appreciated by those familiar with the cotton industry, prices for raw cotton depend in large measure upon the grades thereof. Therefore, it is important that representative samples be taken from each bale in order to determine price before the bale is finally purchased.

Heretofore, one technique employed in obtaining samples requires that samples be cut from the bales as the bales arrive at a warehouse. Often the cuts are made far deeper than necessary for obtaining suitable samples. The resulting open wounds in the bales not only give rise to pilferage but destroy appearance and present a substantial fire hazard.

Machines capable of extracting a sample of raw cotton every fifteen to thirty seconds during baling operations have been employed with varying degrees of success. However, the machines currently available for this purpose are of a rather complex design which result in increased purchase price and maintenance costs.

It is, therefore, the general purpose of the instant invention to provide for use in an automatic sampler a pneumatic condenser through which simplicity in design, efficiency in operation, and reduction in total costs are achieved.

OBJECTS AND SUMMARY OF THE INVENTION

It is an object of the instant invention to provide an improved pneumatic condenser for use in the processing of raw cotton.

It is another object to provide an improved condenser having particular utility in raw cotton samplers capable of taking a sample every fifteen to thirty seconds during baling operations.

It is another object to provide an improved, economic, and practical pneumatic condenser particularly suited for use in an automatic sampler for periodically extracting raw cotton from a delivery conduit as the cotton is delivered to a bale press, whereby necessity of manually cutting bales to effect sampling is avoided.

Another object is to provide a pneumatic condenser having particular utility in automatic samplers for use in periodically sampling raw cotton as the cotton is delivered to a bale press, although not necessarily restricted in use thereto since the pneumatic condenser may be found to be similarly useful when employed in handling raw cotton and the like for purposes other than in the sampling of cotton, as will become more readily apparent by reference to the following description and claims in light of the accompanying drawings.

BRIEF DESCRIPTION OF THE DRAWINGS

FIG. 1 is a perspective view of an automatic sampler, including a pneumatic condenser which embodies the principles of the instant invention.

FIG. 2 is a cross-sectional view taken generally along line 2—2 of FIG. 1.

FIG. 3 is a fragmented view illustrating one of two grates included within the condenser.

FIG. 4 is a diagrammatic view of a control circuit for the condenser.

DESCRIPTION OF THE PREFERRED EMBODIMENT

Referring now, with more particularity, to the drawings wherein like reference numerals designate like or corresponding parts throughout the several views, there is shown in FIG. 1 a perspective view of an automatic sampler having included therein a pneumatic condenser, generally designated 10, which embodies the principles of the instant invention.

The term condenser, as herein employed, refers to an apparatus suited for handling raw cotton. As illustrated in the drawings, the condenser 10 is included within an automatic cotton sampling machine, the purpose of which is to extract samples every fifteen to thirty seconds from a stream of raw cotton as it is delivered to a bale press.

The condenser 10 includes an extractor tube 12 adapted to be connected in communication with a conduit, not designated, employed in delivering a continuous stream of raw cotton from ginning saws to a bale press. The particular configuration of the conduit employed in delivering the raw cotton forms no specific part of the instant invention and is varied as desired. Therefore, a detailed description of the conduit is omitted in the interest of brevity.

Within the extractor tube 12 there is included a pivotal gate 14 suitably supported to be displaced periodically for purposes of opening and closing the extractor tube. Thus delivery of raw cotton through the tube 12 is controlled.

The extractor tube 12 also is connected to communicate with a chute 16. This chute includes a vertically oriented base segment 18, an inclined segment 20 and a horizontally oriented terminal segment 22, FIG. 2, connected in communication with the extractor tube 12.

Within the inclined segment 20 there is provided a pneumatic catcher 24. The function of the catcher 24 is to capture batches of raw cotton serially delivered thereto through the extractor tube 12, as the pivotal gate 14 is periodically pivoted to an open position for placing the catcher in direct communication with the conduit. Upon a closing of the pivotal gate 14, the extractor tube 12 is closed for thus pneumatically isolating the catcher 24 from the conduit, and, hence, from the stream of raw cotton.

The catcher 24 includes a grate 26 having a configuration as illustrated in FIG. 3. The grate 26 includes one face preferably disposed in coplanar relationship with one wall of the inclined segment 20 of the chute 16. Thus the grate provides a surface which accommodates passage of raw cotton through the chute.

Disposed in communication with the opposite face of the grate 26 there is a vacuum chamber 28, of a substantially truncated conical configuration, as best illustrated in FIG. 2. The vacuum chamber 28, in response to a vacuum introduced therein, serves to introduce a vacuum into the chute 16. Such a vacuum is, therefore, available for extracting raw cotton from the aforementioned conduit so long as the first gate 14 is in an open position and the grate 26 communicates with the conduit. Of course, raw cotton thus introduced into the chute 16 is captured by the catcher 24 and held on the face of the grate 26, due to the low-pressure effects of the vacuum maintained in the chamber 28 and applied to both surfaces of the grate 26. Within the chute 16, between the catcher 24 and the base segment 18 thereof there is provided a pivotal chute closure gate 30. This gate, when closed, serves to prevent passage of raw cotton through the chute 16. Moreover, the gate remains closed so long as the vacuum chamber 28 functions to apply a vacuum to the grate 26, whereby the vacuum is isolated from the base segment 18 of the chute.

The base segment 18 of the chute 16, as best shown in FIG. 2, is substantially vertically oriented and terminates in a chamber 31 which serves to receive raw cotton delivered thereto through the chute 16 to be compressed prior to delivery to a sample bale, not shown.

Compression of the raw cotton within the chamber 31 is achieved through a use of a vertically reciprocated foot 32 of a tramper 34. The tramper includes a shaft 35 to which the foot is attached projected downwardly from a pneumatic cylinder 36 into the base segment 18 for the chute 16. It is to be understood that the cylinder 36 is supported in a suitable manner and adapted to be pressurized reversely for imparting reciprocation to the shaft 35, whereupon the foot 32 is advanced along a rectilinear path toward and away from the chamber 31 for periodically compressing cotton confined in the chamber.

The base segment 18 of the chute 16 also includes a grate, designated 38. The grate 38 is suitably supported in communication with a vacuum chamber 40, also of a substantially truncated conical configuration. Thus the vacuum chamber 40 also communicates with the chute 16. Consequently, a vacuum introduced into the vacuum chamber 40 also is introduced into the chute 16, via the base segment 18.

The vacuum chambers 28 and 40 each communicate with a vacuum source 42. This source comprises a suitable design and alternately communicates with the chambers 28 and 40 through a common flapper valve, generally designated 43. The flapper valve 43 includes a valve chamber 44 within which there is supported a pivotal flapper valve gate 46. The flapper valve gate 46 is a displaceable gate which, when in a first direction, places the vacuum chamber 28 in direct communication with the vacuum source 42. Alternatively, when the gate is pivotally displaced to its alternate position, the vacuum chamber 40 is placed in direct communication with the vacuum source 42. Through an alternate positioning of the gate 46 it is possible to alternately introduce vacuums in the chambers 28 and 40, drawn down by the source 42.

The gate 14 is supported for pivotal displacement by a suitable pin, not designated, connected with a pneumatic actuator 48. Connection between the gate and the actuator is made through a suitable bell crank linkage 50. The chute closure gate 30 also is supported by a suitable axle, also not designated, connected with a pneumatic actuator 52 through a suitable bell crank 54. The gate 46 of the flapper valve 43 also is supported by a suitable axle, also not designated, connected with a pneumatic actuator 56 through a suitable bell crank, designated 58. Therefore, it should be apparent that operation of the condenser 10 is controlled through a selective pressurization of the cylinder 36, and the actuators 48, 52 and 56. Preferably, the actuators 48, 52 and 56 comprise spring-loaded pneumatic actuators of known design.

The cylinder 36 and actuators 48, 52 and 56 are connected for pressurization to a suitable source of air 60, schematically illustrated in FIG. 5. Suitable conduits, not designated, are provided for connecting the cylinder and actuators with a suitable selector valve 62. The selector valve is of a suitable design which accommodates a selective coupling of the cylinder 36 and the actuators 48, 52 and 56 with the source of air, designated 60. While not shown, it is to be understood that the selector valve includes a multiplicity of valve components connected with a multiplicity of solenoids, also not shown. The solenoids are, in turn, controlled by a suitable control circuit, designated 64. The control circuit 64 is, in turn, connected with a suitable source of electrical potential. The circuit includes components which are selectively energized in a timed relationship with a bale press to which the stream of raw cotton is delivered. The specific control circuit employed forms no part of the instant invention and the components thereof are varied as desired to achieve desired results.

It is important, therefore, to appreciate that the circuitry depicted in FIG. 5 is illustrative of suitable circuitry, and it is intended that the schematic illustration of the circuitry shown in FIG. 5 not be considered exclusive of other suitable circuitry which can be employed equally as well in controlling the operation of the condenser 10. Moreover, where desired, it is possible to operate the condenser 10 satisfactorily in the absence of the aforementioned actuator 52, since in operation a vacuum necessarily is applied to the opposite faces of the closure gate 30, and the effect of the vacuum thus applied can be relied upon to pivotally displace the gate 30.

Additionally, a transparent window 66 is provided, where desired, for affording operators opportunity to visually inspect the catcher 24, whereby clean-out of the chute 16 is accommodated.

OPERATION

It is believed that in view of the foregoing description, the operation of the device will readily be understood and it will be briefly reviewed at this point.

With the extractor tube 12 connected with a selected conduit, adapted to deliver a stream of raw cotton, the chute closure gate 30 positioned in a closed position, so as to substantially establish a seal between the segments 18 and 20 of the chute 16, the pivotal gate 14 closed, in order to isolate the chute 16 from the extractor tube 12, and the foot 32 supported in an elevated condition, the condenser is prepared for a cycle of operation.

A vacuum is now introduced into the vacuum chamber 28, from the source 42, simply by activating the source 42. As a consequence of a vacuum being t  s introduced in the vacuum chamber 28, a vacuum also is introduced into the chute 16, via the apertures formed in the grate 26. Thus a vacuum is established within the chute 16.

A signal now is delivered from the control circuit 64 to the selector valve 62 for thus causing the actuator 48 to be selectively pressurized, for thereby causing the tube closure gate 14 to pivot to an open position, whereby the extractor tube 12 is established between the grate 26 and the conduit to which the extractor tube 12 is connected. Consequently, a batch of raw cotton is now drawn from the conduit via the terminal segment 22 of the chute 16 and captured at the catcher 24, as a consequence of the vacuum applied through the apertures of the grate 26. So long as a vacuum is maintained within the chamber 28, the raw cotton is held in place against the surface of the grate 26.

Following a period of a predetermined duration, the pressure within the actuator 48 is released for causing the closure gate 14 to return to a tube closing disposition, whereupon delivery of cotton from the conduit is interrupted. Thus a batch of raw cotton is extracted from the conduit.

An electrical signal is now delivered from the control circuit 64 to the selector valve 62, for thus causing the actuator 56 to be pressurized whereupon the gate 46 of the flapper valve 43 pivots upwardly. Such pivotal motion of the gate 46 serves to interrupt communication between the vacuum chamber 28 and the source of vacuum 42 while simultaneously establishing communication between the vacuum chamber 40 and the source 42. Thus the vacuum within the chamber 28 is interrupted and a vacuum is introduced into the vacuum chamber 40.

The vacuum thus introduced into the vacuum chamber 40 is also introduced into the base segment 18 of the chute 16, via apertures of the grate 38. Substantially simultaneously with the pneumatic energization of the actuator 56, energization of the actuator 52 is similarly achieved in response to a signal delivered from the control circuit 64 to the selector valve 62. Thus the chute closure gate 30 is pivotally displaced into a chute opening disposition so that the vacuum introduced into the base segment 18 of the chute 16 is simultaneously introduced into the inclined segment 20 of the chute 16. It will, of course, be appreciated that the vacuum thus introduced into the incline segment 20 of the chute 16 serves to displace the batch of cotton supported by the catcher 24, downwardly into the base segment 18 of the chute.

Once the batch of raw cotton enters the base segment 18 of the chute 16, the chute closure gate 30 is permitted to return to its initial position, through a selective depressurization of the actuator 52. Simultaneously, a repositioning of the flapper valve gate 46 to its initial position is similarly effected so that the vacuum established within the vacuum chamber 40 is terminated. A release of raw cotton from the surface of the grate 38 is thereby achieved. At substantially this instant in time, the cylinder 36 is energized for driving the foot 32 downwardly into the base segment 18 of the chute for compressing the raw cotton within the chamber 31. The foot 32 is then elevated to its initial position, through a reversed pressurization of the cylinder 36. The condenser is now prepared to be recycled for extracting another batch of raw cotton from the conduit.

In view of the foregoing, it should readily be apparent that the condenser which embodies the principles of the instant invention provides a practical, simple, and economic device having particular utility in periodically sampling raw cotton as the cotton is delivered from gin saws to a bale press.

Although the invention has been herein shown and described in what is conceived to be the most practical and preferred embodiment, it is recognized that departures may be made therefrom within the scope of the invention, which is not to be limited to the illustrative details disclosed.

Having described my invention, what I claim as new and desire to secure by Letters Patent is:

1. In an automatic sampler particularly suited for use in periodically sampling raw cotton as the cotton is delivered to a bale press through a conduit and characterized by an extractor tube connected to said conduit and employed for periodically extracting batches of raw cotton from the conduit, a pneumatic condenser comprising:

extraction means for periodically extracting a batch of raw cotton from a stream of raw cotton passing through the conduit, including a pneumatic catcher communicating with said extractor tube for serially collecting each extracted batch of raw cotton, and pneumatic means for serially delivering each batch of raw cotton from said catcher to a sample press.

2. The condenser of claim 1 wherein said condenser further comprises means for evacuating said extractor tube, whereby said batches of raw cotton are pneumatically extracted from said conduit.

3. The condenser of claim 1 wherein said extraction means further includes a normally closed pivotal door mounted in said extractor tube between said conduit and said catcher for interrupting communication therebetween, and means for periodically pivoting said door to an open position for placing said catcher in communication with said conduit.

4. The condenser of claim 3 wherein said extraction means further includes a source of vacuum, and means for placing said catcher in communication with said source of vacuum.

5. The condenser of claim 4 wherein said catcher includes a grate and said means for placing the catcher in communication with said source of vacuum includes means for alternatively subjecting the opposite faces of the grate to a vacuum.

6. The condenser of claim 5 wherein the pneumatic means for serially delivering each batch of raw cotton to a sample press includes a delivery chute extended between said catcher and the sample press, and the means for alternately subjecting the opposite faces of the grate to a vacuum includes a first vacuum chamber communicating with said grate at one face thereof, and a second vacuum chamber communicating with the other face of the grate through the chute, and gate means for alternately connecting the chambers with said source of vacuum.

7. A pneumatic condenser particularly suited for use in delivering raw cotton to a press comprising:

A. an extractor tube through which raw cotton is delivered including a first pivotal gate mounted therein for controlling the flow of cotton therethrough and means for periodically repositioning said gate means from a closed position to an opened position, whereby the tube is periodically opened for accommodating passage of raw cotton therethrough;

B. a pneumatic catcher communicating with said tube for collecting raw cotton delivered through said tube, including a grate and a first vacuum chamber connected in communication with one face of said grate;

C. means for delivering raw cotton from the catcher including a delivery chute extending from the catcher to a cotton press;

D. a second vacuum chamber connected in communication with the other face of said grate through said delivery chute;

E. a source of vacuum;

F. a second pivotal gate interposed between said source of vacuum and said first and second vacuum chambers for alternately connecting the chambers in communication with said source of vacuum; and
G. circuit means for controlling operation of said gate means.

8. The condenser of claim 7 wherein the means for delivering raw cotton from the catcher further includes a third pivotal gate interposed between the pneumatic catcher and the second vacuum chamber and means for selectively pivoting said third gate from a closed position to an open position for controlling delivery of raw cotton from said catcher.

* * * * *

UNITED STATES PATENT AND TRADEMARK OFFICE
Certificate

Patent No. 3,987,678                          Patented October 26, 1976

Jack L. Gable

Application having been made by Jack L. Gable, the inventor named in the patent above identified, and Superior Cotton Sampling, Inc., a corporation of California, the assignee, for the issuance of a certificate under the provisions of Title 35, Section 256, of the United States Code, adding the name of Noil E. Breedlove as a joint inventor, and a showing and proof of facts satisfying the requirements of the said section having been submitted, it is this 17th day of May 1977, certified that the name of the said Noil E. Breedlove is hereby added to the said patent as a joint inventor with the said Jack L. Gable.

FRED W. SHERLING,
*Associate Solicitor.*